(12) United States Patent
Hou et al.

(10) Patent No.: US 11,333,592 B2
(45) Date of Patent: May 17, 2022

(54) RUBBER WEAR TESTING DEVICE

(71) Applicant: The Yokohama Rubber Co., LTD., Tokyo (JP)

(72) Inventors: Gang Hou, Hiratsuka (JP); Susumu Hatanaka, Hiratsuka (JP)

(73) Assignee: The Yokohama Rubber Co., LTD., Tokyo (JP)

( * ) Notice: Subject to any disclaimer, the term of this patent is extended or adjusted under 35 U.S.C. 154(b) by 672 days.

(21) Appl. No.: 16/316,176

(22) PCT Filed: Feb. 27, 2017

(86) PCT No.: PCT/JP2017/007439
§ 371 (c)(1),
(2) Date: Jan. 8, 2019

(87) PCT Pub. No.: WO2018/012022
PCT Pub. Date: Jan. 18, 2018

(65) Prior Publication Data
US 2021/0293680 A1    Sep. 23, 2021

(30) Foreign Application Priority Data
Jul. 12, 2016 (JP) .............................. JP2016-137239

(51) Int. Cl.
*G01N 3/56* (2006.01)
*G01N 33/44* (2006.01)

(52) U.S. Cl.
CPC ............. *G01N 3/56* (2013.01); *G01N 33/445* (2013.01)

(58) Field of Classification Search
None
See application file for complete search history.

(56) References Cited

U.S. PATENT DOCUMENTS

| 1,711,866 | A | * | 5/1929 | Williams | ................. | G01N 3/56 73/7 |
| 3,388,584 | A | * | 6/1968 | Velde | ........................ | G01N 3/56 73/7 |
| 3,899,917 | A | * | 8/1975 | Kisbany | ................... | G01N 3/56 73/8 |
| 4,995,197 | A | * | 2/1991 | Shieh | ...................... | B24B 5/366 451/1 |

(Continued)

FOREIGN PATENT DOCUMENTS

| CN | 102735559 | 10/2012 |
| CN | 202735182 | 2/2013 |

(Continued)

OTHER PUBLICATIONS

International Search Report for International Application No. PCT/JP2017/007439 dated Apr. 11, 2017, 4 pages, Japan.

*Primary Examiner* — Daniel S Larkin
(74) *Attorney, Agent, or Firm* — Thorpe North & Western

(57) ABSTRACT

Provided is a rubber wear testing device including a holding portion for holding a test sample of rubber, and a compression bonding mechanism for applying an additional force oriented to a circular circumferential surface of a rotation body rotating such that the test sample is pressed to the circular circumferential surface at a predetermined fixed position and the movement of the test sample in a direction opposite to the additional force is always allowed.

14 Claims, 6 Drawing Sheets

(56) References Cited

U.S. PATENT DOCUMENTS 6,412,330 B1* 7/2002 Dicello .................. G01N 3/56
73/7
2017/0284915 A1 10/2017 Hou

FOREIGN PATENT DOCUMENTS

| | | |
|---|---|---|
| JP | S64-053951 | 4/1989 |
| JP | H02-210243 | 8/1990 |
| JP | 2002-181609 | 6/2002 |
| JP | 2004-037286 | 2/2004 |
| JP | 2009-198276 | 9/2009 |
| JP | 2013-113672 | 6/2013 |
| JP | 2013-178163 | 9/2013 |
| JP | 2016-061597 | 4/2016 |
| JP | 2016-090417 | 5/2016 |
| WO | WO 2016/042998 | 3/2016 |

* cited by examiner

RUBBER WEAR TESTING DEVICE

TECHNICAL FIELD

The present technology relates to a rubber wear testing device, and more particularly relates to a rubber wear testing device capable of easily determining the wear state of rubber with higher accuracy in accordance with practical use.

BACKGROUND ART

As a tester for evaluating rubber wear resistance, a DIN (German Institute for Standardization) abrasion tester and a Williams abrasion tester have been known in the related art. However, it is an object of these abrasion testers to determine wear resistance under a constant condition that has been preset. Thus, these abrasion testers fail to set conditions in conformity with various operating environments of a conveyor belt and have difficulty in estimating the wear resistance of the upper cover rubber of the conveyor belt with accuracy in practical use.

Accordingly, there has been proposed a wear testing device using an annular belt sample and a mechanism similar to a belt conveyor device (see Japan Unexamined Patent Publication No. 2016-90417). According to this testing device, tests can be performed under conditions similar to the actual operating conditions of the conveyor belt, and thus it is advantageous to determine the wear resistance of the upper cover rubber with accuracy. However, an annular belt sample is necessary, and the structure of the testing device is complicated.

Incidentally, when a target object and a rubber move relatively in contact with each other, and the target object slides to the rubber, both are not uniformly in contact with each other. In a stick-slip phenomenon, a process (sticking process) in which the rubber counteracts a force (frictional force) received from the target object and is elastically deformed, and a process (slippage process) in which the rubber cannot counteract the frictional force and elastic deformation is released, and the rubber is slid to the target object, are repeated. In the testing devices in the related art, the stick-slip phenomenon is not sufficiently taken into consideration, and thus there is room for improvement to determine the wear state of rubber with accuracy.

SUMMARY

The present technology provides a rubber wear testing device capable of easily determining the wear state of rubber with accuracy in accordance with practical use.

A rubber wear testing device of the present technology includes a holding unit configured to hold a test sample of rubber, a rotation body including a circular circumferential surface in contact with the test sample, a drive unit configured to drive and rotate the rotation body, and a compression bonding mechanism configured to apply an additional force oriented to the circular circumferential surface to the test sample held by the holding unit and always allow the movement of the test sample in a direction opposite to the additional force. The test sample held by the holding unit with respect to the rotation body being driven and rotated is configured to be compressed and bonded to the circular circumferential surface at a predetermined fixed position.

According to the present technology, the additional force oriented to the circular circumferential surface of the rotation body being driven and rotated is applied to the test sample held by the holding portion by using the compression bonding mechanism, the test sample is compressed and bonded to the circular circumferential surface at a predetermined fixed position, and the movement of the test sample in the direction opposite to the additional force is always allowed, thereby reproducing the stick-slip phenomenon. Accordingly, the wear state of rubber in accordance with practical use can be determined with higher accuracy without using an annular rubber sample or a device having a complicated structure.

DETAILED DESCRIPTION

Hereinafter, a rubber wear testing device according to the present technology will be described based on embodiments illustrated in drawings.

Figure 1:
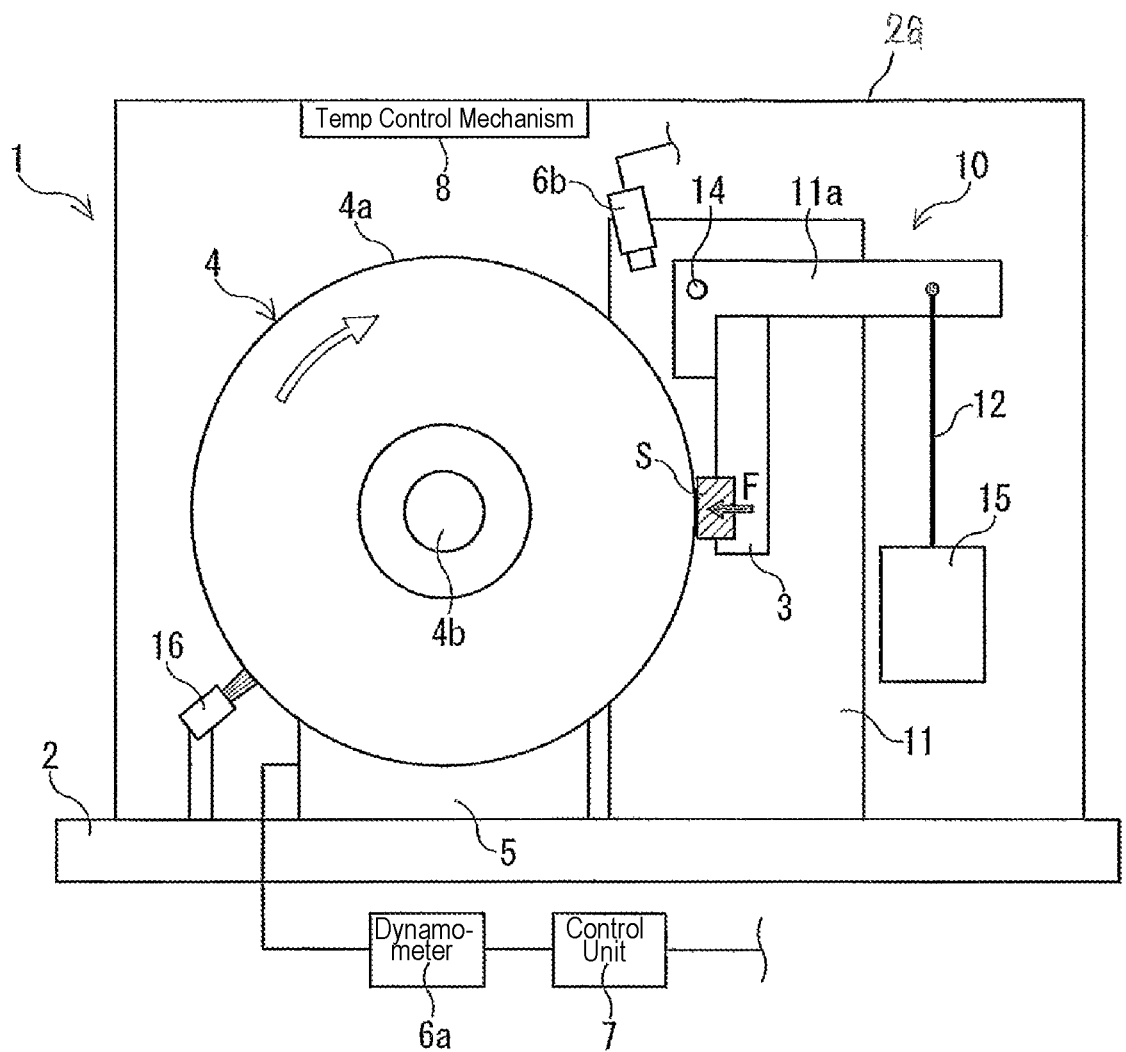
FIG. 1 is an explanatory diagram illustrating a wear testing device in a front view according to the present technology.
Figure 2:
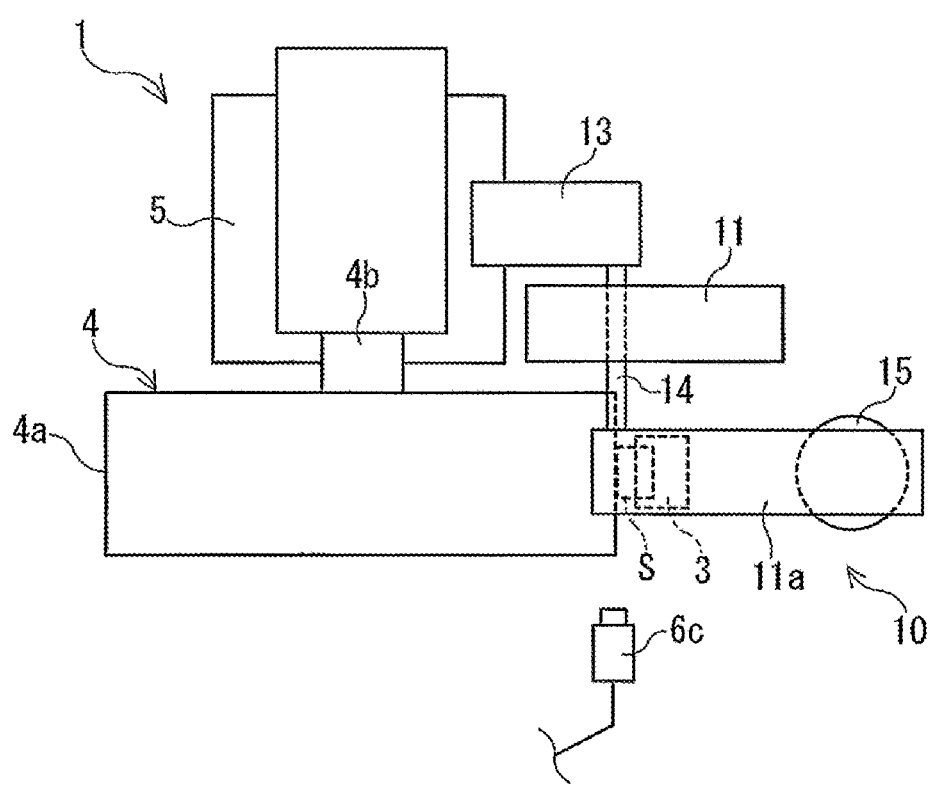
FIG. 2 is an explanatory diagram illustrating part of the wear testing device in FIG. 1 in a plan view.

In a rubber wear testing device 1 of the present technology illustrated in FIGS. 1 and 2, a rubber test sample S to be tested is only required to use a block-shaped mass or the like, not an annular body. The testing device 1 includes a holding portion 3 for holding the test sample S, a rotation body 4, a drive unit 5 for driving and rotating the rotation body 4, and a compression bonding mechanism 10. The wear testing device 1 of the embodiment further includes a dynamometer 6a, a temperature sensor 6b, a camera 6c, a control unit 7, a temperature control mechanism 8, and a scraper 16, and components except for the dynamometer 6a and the control unit 7 are covered with a casing 2a installed on a base 2.

The holding portion 3 removably holds the test sample S. The holding portion 3 is not limited to a single one, and a plurality of holding portions 3 may be provided.

The rotation body 4 is a columnar or cylindrical grinding wheel and includes a circular circumferential surface 4a in contact with the test sample S. The circular circumferential surface 4a serves as a grinding surface with respect to the test sample S. The rotation body 4 is rotatable around a rotation shaft 4b provided in the center of the circle thereof.

As for a material or surface roughness of the circular circumferential surface 4a or the like, appropriate specifications are selected based on test conditions. For example, a plurality of rotation bodies 4, each circular circumferential surface 4a of which has a different specification, is prepared, and the rotation bodies 4 are configured to be replaced in accordance with the specification of a necessary circular circumferential surface 4a. Alternatively, the rotation body 4 may be provided such that only the circular circumferential surface 4a is replaceable. In this case, the circular circumferential surface 4a corresponding to a necessary specification is mounted on the core of the rotation body 4.

The drive unit 5, for example, is a drive motor and is connected to the control unit 7. A rotational speed of the rotation body 4 (rotation shaft 4b) is controlled to be a desired speed by the control unit 7. In this embodiment, the drive unit 5 and the control unit 7 are connected via the dynamometer 6a. The dynamometer 6a measures energy (e.g., power consumption of the drive motor 5) required for driving and rotating the rotation body 4. Measurement data of the dynamometer 6a is input and stored in the control unit 7.

The compression bonding mechanism 10 applies the additional force F oriented to the circular circumferential surface 4a to the test sample S held by the holding portion 3. This causes the test sample S held by the holding portion 3 to be compressed and bonded to the circular circumferential surface 4a at a predetermined fixed position with respect to the rotation body 4 being driven and rotated. The compression bonding mechanism 10, further, is configured to allow the movement of the test sample S in a direction opposite to the additional force F at all times.

Specifically, the compression bonding mechanism 10 of the present embodiment is constituted of an L-shaped holding arm 11a coupled with the holding portion 3, a wire 12 whose one end is connected to the holding arm 11a, and a weight 15 connected to the other end of the wire 12. A support shaft 14 arranged in parallel to the rotation shaft 4b of the rotation body 4 penetrates a supporting column 11 installed upright on the base 2 and is rotatably supported. The holding arm 11a is fixed to one end portion of the support shaft 14, and a balancer 13 is fixed to the other end portion.

The weight of the weight 15 acts on the holding arm 11a via the wire 12. Thus, the holding portion 3 integrated with the holding arm 11a by the tension of the wire 12 rotates with the test sample S around the support shaft 14. That is, the weight of the weight 15 acts on the test sample S held by the holding portion 3, thereby applying the additional force F oriented to the circular circumferential surface 4a to the test sample S.

The magnitude of the additional force F can be easily changed by varying the weight of the weight 15. Alternatively, the magnitude of the additional force F can be changed by varying a horizontal distance between the supporting shaft 14 and the connection position of the wire 12 with respect to the holding arm 11a, or varying the weight of a balancer 13. Further, the balancer 13 can be installed in such a manner that the additional force F reaches zero in a state where the weight 15 is removed. For example, the weight of the balancer 13 and a distance from the supporting shaft 14 are selected in such a manner that the empty weight of the compression bonding mechanism 10 in a state where the weight 15 is removed is cancelled out, thereby causing the additional force F to reach zero. The weight of weight 15 and the additional force F can be equated by installing the balancer 13 in such a manner that the additional force F reaches zero in a state where the weight 15 is removed, and by equating the distance between the test sample S and the supporting shaft 14 with the distance between the supporting shaft 14 and the connection position of the wire 12 with respect to the holding arm 11a.

The surface of the test sample S opposite to the circular circumferential surface 4a is brought into a state of being pressed against and in contact with the circular circumferential surface 4a by the additional force F (specified load) having a constant magnitude all the time. It is preferable that the direction of the additional force F is set to a direction oriented to the rotation center (rotation shaft 4b) of the rotation body 4. With this direction, the test sample S can be stably pressed and in contact with the circular circumferential surface 4a by the additional force F. To facilitate the smooth rotation of the holding arm 11a around the support shaft 14, for example, the support shaft 14 may be supported by the supporting column 11 via a bearing.

Herein, the test sample S is simply pressed against the circular circumferential surface 4a based on the weight of the weight 15. Thus, the holding arm 11a rotates around the support shaft 14, which makes it possible for the test sample S to move in the direction opposite to the additional force F all the time. Along with this, when a force in the direction opposite to the additional force F acts on the test sample S, the test sample S can move in the direction in which the test sample S separates from the circular circumferential surface 4a.

The compression bonding mechanism 10 is not limited to the configuration illustrated in the embodiment. As long as the compression bonding mechanism 10 has the configuration in which the additional force F oriented to the circular circumferential surface 4a is applied to the test sample S held by the holding portion 3, thereby being compressed and bonded to the circular circumferential surface 4a at a predetermined fixed position, and the movement of the test sample S in the direction opposite to the additional force F is always allowed, various configurations can be employed.

In this embodiment, the test sample S is in contact with the circular circumferential surface 4a at the same position as that of the rotation shaft 4b on the horizontal level, but the position (position in the circumferential direction of the rotation body 4) at which the test sample S is in contact with the circular circumferential surface 4a is not limited to this. For example, a configuration in which the test sample S is in contact with the circular circumferential surface 4a at a position above the rotation shaft 4b may be applied. Thus, a predetermined fixed position at which the test sample S is compressed and bonded to the circular circumferential surface 4a can be set as appropriate.

The temperature sensor 6b detects the temperature of at least one of the circular circumferential surface 4a or the test sample S. The detection data of the temperature sensor 6b is input and stored in the control unit 7. The camera 6c takes a photograph of the movement of the test sample S, and the photographed video data is input and stored in the control unit 7.

The temperature control mechanism 8 adjusts the test sample S to a predetermined temperature. In this embodiment, the temperature control mechanism 8 is provided on the upper surface of the casing 2a. The internal temperature of the casing 2a is adjusted to the predetermined temperature by the temperature control mechanism 8, which indirectly adjusts the temperature of the test sample S.

The temperature control mechanism 8 is controlled by the control unit 7. A heater that directly heats the test sample S or a cooler that directly cools the test sample S can be employed as the temperature control mechanism 8.

The scraper 16, for example, has a brush shape and is in contact with the circular circumferential surface 4a. In this embodiment, the scraper 16 is in contact with the circular circumferential surface 4a at a position on a side opposite to the test sample S with the rotation shaft 4b sandwiched therebetween.

Figure 5:
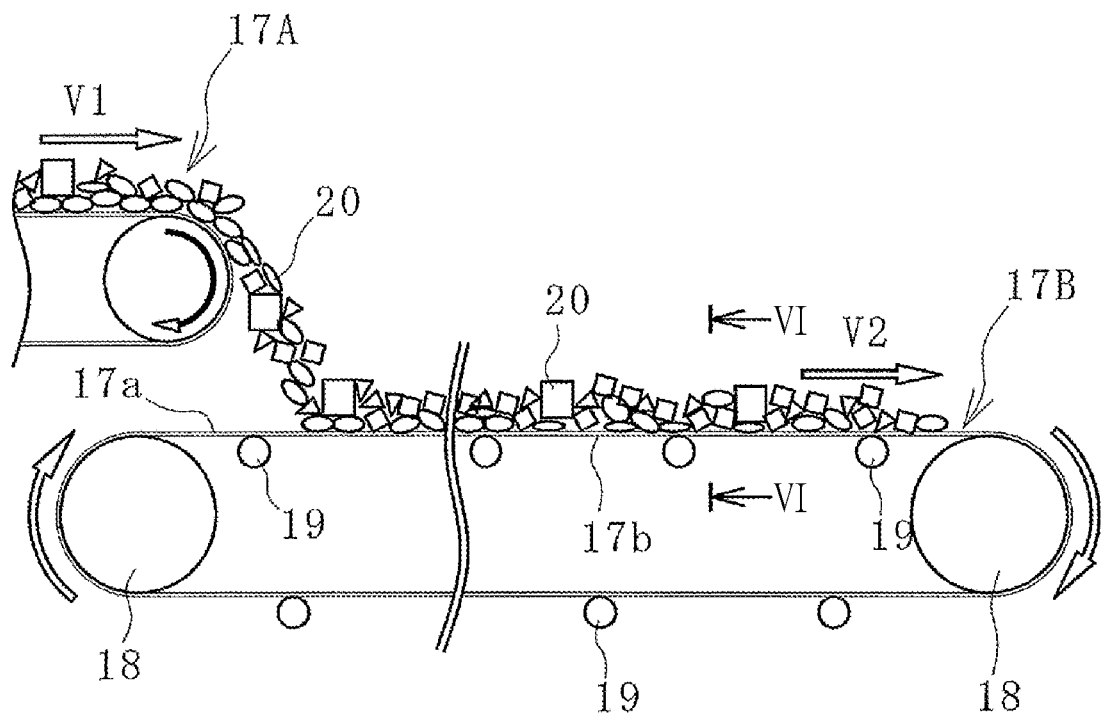
FIG. 5 is an explanatory diagram illustrating a simplified conveyor belt line.
Figure 6:
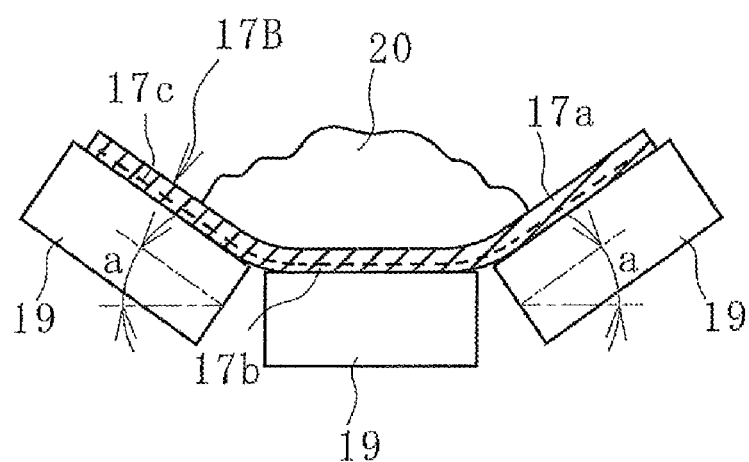
FIG. 6 is a cross-sectional view taken along line VI-VI in FIG. 5.

Incidentally, in the actual conveyor belt line, as illustrated in FIGS. 5 and 6, objects 20 to be conveyed by a conveyor belt 17A are fed onto another conveyor belt 17B and conveyed to a conveying destination. The conveyor belt 17B is looped on pulleys 18 and mounted under predetermined tension.

The conveyor belt 17B is constituted of a core body layer 17c constituted of a core body such as a canvas, a steel cord, or the like, and an upper cover rubber 17a and a lower cover rubber 17b that sandwich the core body layer 17c. The core body layer 17c maintains tension to mount the conveyor belt 17B. The lower cover rubber 17b is supported by a support roller 19 on a carrying side of the conveyor belt 17B, and the upper cover rubber 17a is supported by the support roller 19 on a return side of the conveyor belt 17B. For example, three support rollers 19 are arranged in a belt width direction on the carrying side of the conveyor belt 17B, and the conveyor belt 17B is supported by the support rollers 19 in a recessed shape at a predetermined trough an angle a.

Typically, the objects 20 to be conveyed are fed from the conveyor belt 17A, whose travel speed V1 is relatively low, to the conveyor belt 17B, whose travel speed V2 is relatively high (travel speed V1<travel speed V2). The speed of the objects 20 to be conveyed that have been fed changes from the travel speed V1 to the travel speed V2 on the upper cover rubber 17a of the conveyor belt 17B. Thus, the objects 20 to be conveyed slide with respect to the upper cover rubber 17a, and this sliding constitutes the main factor and causes the upper cover rubber 17a to be worn.

Figure 3:
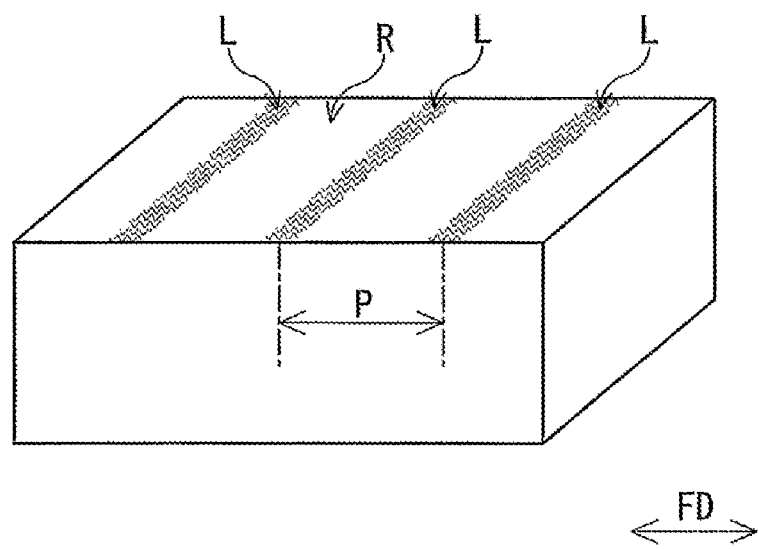
FIG. 3 is an explanatory diagram illustrating a stick-slip phenomenon.

Accordingly, when the objects 20 to be conveyed slide with respect to the upper cover rubber 17a, the stick-slip phenomenon occurs. In the stick-slip phenomenon, as described above, the sticking process and the slippage process are repeated, and thus, as illustrated in FIG. 3, wear streaks L with predetermined pitches P in a sliding direction FD are formed on the surface of the rubber R on which the target object slides. The pitches P correspond to the slippage process, and the wear streaks L correspond to the sticking process. In the wear testing device 1 of the present technology, it is possible to reproduce the stick-slip phenomenon.

Hereinafter, a method for determining the wear state of rubber using the wear testing device 1 will be described.

As illustrated in FIGS. 1 and 2, the test sample S is held by the holding portion 3. A desired specification is set for the circular circumferential surface 4a. For example, when an upper cover rubber 17a of a conveyor belt as the test sample S is evaluated, the circular circumferential surface 4a having surface roughness in conformity with the shape of a conveyance object 20 conveyed on the conveyor belt, or the like is used. In addition, the weight of the weight 15 is set in such a manner that a desired additional force F is applied to the test sample S, and the rotation body 4 is rotated at the desired speed having been set. Further, the temperature control mechanism 8 is activated, thereby setting the test sample to a desired temperature. The settings, for example, are performed in accordance with conditions under which the rubber of the test sample S is practically used.

In the wear testing device 1 with the settings described above, the additional force F oriented to the circular circumferential surface 4a of the rotation body 4 rotating is applied to the test sample S as illustrated in FIG. 1. The test sample S is pressed by the additional force F at a predetermined fixed position with respect to the rotation body 4 and comes in contact with the circular circumferential surface 4a. The rotation body 4 is rotating, which brings the test sample S and the circular circumferential surface 4a into a state of sliding, and thus the contact surface with the circular circumferential surface 4a of the test sample S is gradually worn.

After a predetermined test time, the measurement of the amount of wear or the wear surface of the test sample S is observed. In addition, the surface roughness of the test sample S is compared before and after the test, and a wear state of the test sample S is comprehensively determined.

Herein, in the present technology, the movement of the test sample S is always allowed in the direction opposite to the additional force F. Consequently, as for the test sample S sliding on the circular circumferential surface 4a, the process (sticking process) in which the test sample S counteracts frictional force on the circular circumferential surface 4a and is elastically deformed, and the process (slippage process) in which the test sample S cannot counteract the frictional force and elastic deformation is released, and the test sample S is slid to the circular circumferential surface 4a, can be repeated. That is, the stick-slip phenomenon is reproduced.

In contrast, when the additional force F is configured to be applied to the test sample S by a fluid cylinder or the like, there is no room for the test sample S to move in the direction opposite to the additional force F, and thus the test sample S is brought into a state of being adhered to the circular circumferential surface 4a all the time. Therefore, the sticking process and the slippage process cannot be repeated, and the stick-slip phenomenon cannot be reproduced.

According to the present technology, the stick-slip phenomenon can be reproduced, so that it is possible to determine the wear state of rubber with higher accuracy in accordance with practical use. In particular, it is favorable to determine the wear state of the upper cover rubber of the conveyor belt.

In addition, a block-shaped small piece or the like may be used as the test sample S, and it is not necessary to prepare an annular body on purpose. Further, it is not necessary to prepare a device having a complicated structure in order to have a configuration in which the additional force F oriented to the circular circumferential surface 4a of the rotation body 4 is applied to the test sample S, thereby causing the test sample S to be compressed and bonded to the circular circumferential surface 4a at a predetermined fixed position, and the movement of the test sample S in the direction opposite to the additional force F is always allowed.

In the present technology, a change in the temperature of at least one of the circular circumferential surface 4a or the test sample S can be detected by the temperature sensor 6b during the test. When the test sample S is worn, thermal energy is generated, and thus the energy in the wearing of the test sample S can be determined based on detection data by the temperature sensor 6b. The magnitude of this energy differs depending on the type of rubber. Therefore, the detection data, for example, is advantageous when determining the type of rubber that is capable of reducing the energy.

Fluctuations in energy can be determined by measuring energy required for driving and rotating the rotation body 4 with the dynamometer 6a. The energy required for driving and rotating the rotation body 4 is relatively increased in the sticking process of the stick-slip phenomenon, and relatively reduced in the slippage process of the stick-slip phenomenon. Thus, the predetermined pitches P in the stick-slip phenomenon of the test sample S can be determined based on the fluctuations in energy detected by the dynamometer 6a. The pitches P differ depending on the type of rubber or test condition, and thus serve as one index to evaluate the wear state of rubber.

In addition, the frictional force acted on the test sample S can be calculated based on the detection data by the dynamometer 6a. For example, energy generated by the friction between the test sample S and the circular circumferential surface 4a can be calculated by comparing the energy required for driving and rotating the rotation body 4 at a predetermined speed in a case where the additional force F is applied to the test sample S, thereby causing the test sample S to be in contact with the circular circumferential surface 4a of the rotation body 4 and in a case where the test sample S is not in contact with the circular circumferential surface 4a of the rotation body 4. That is, a difference in compared energy can be approximated to the energy generated by the friction. Then, since the outer diameter and the rotation speed of the rotation body 4 or the like are known, frictional force acted on the test sample S can be approximately calculated. Consequently, a relation of the additional force F applied to the test sample S and the frictional force can be determined for each type of rubber.

In this embodiment, the behavior of the test sample S in the stick-slip phenomenon can be verified by taking a photograph of the movement of the test sample S with the camera 6c. One cycle of the stick-slip phenomenon in which the sticking process and the slippage process are repeated changes depending on the rotation speed of the rotation body 4 or the type of rubber, and for example, is approximately 0.01 to 0.03 seconds. Thus, a high-speed camera 6c that can shoot 100 frames or more per second is favorably used.

Further, the amount of deformation in the pressing direction of the test sample S can be determined by the shooting data of the camera 6c. Thus, the relation of the amount of deformation of the test sample S and the additional force F and the relation of the amount of deformation and the frictional force can be determined.

The wear resistance of the test sample S has temperature dependency. Thus, the temperature dependency can be determined for each type of rubber by varying the temperature of the test sample S with the temperature control mechanism 8 and performing the test.

In this embodiment, the rotation of the rotation body 4 causes the scraper 16 to remove wear debris or the like of the test sample S adhered to the circular circumferential surface 4a. Consequently, constant surface roughness on the circular circumferential surface 4a is easily maintained all the time, which is much more advantageous to determine the wear state of rubber of the test sample S with accuracy. When a contact position of the scraper 16 on the circular circumferential surface 4a is disposed on the front side in the rotating direction of the rotation body 4 with respect to the test sample S and disposed at a lower place as much as possible, the wear debris or the like that has been removed can be prevented from scattering.

Figure 4:
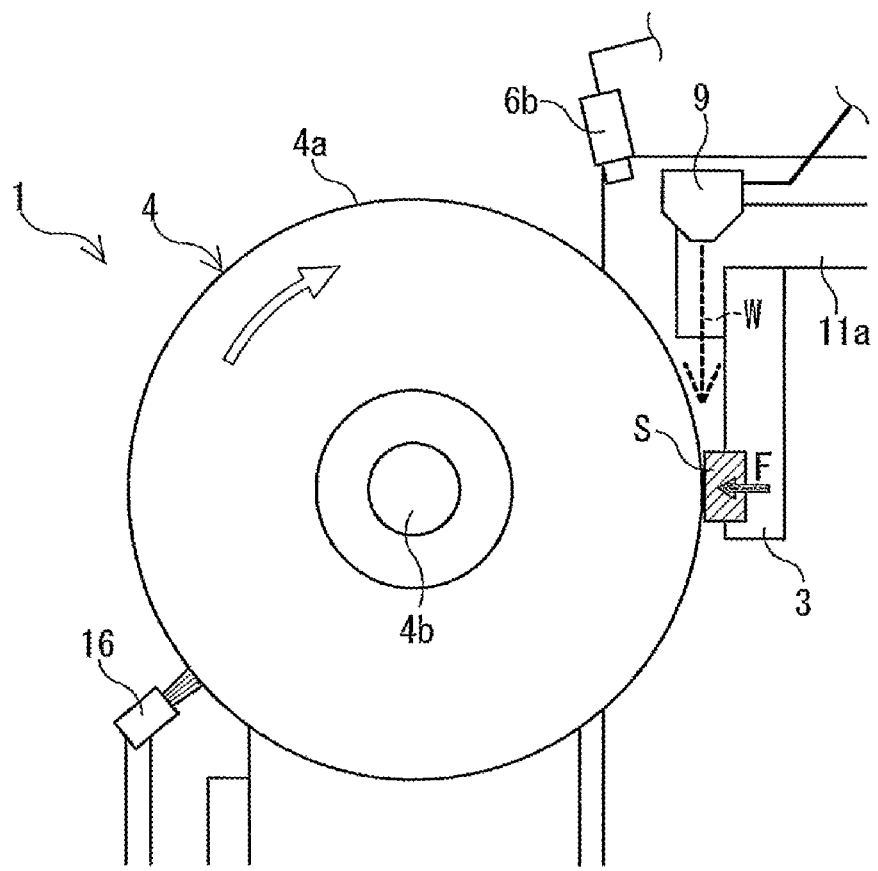
FIG. 4 is an explanatory diagram illustrating part of a configuration of a wear testing device of another embodiment in a front view.

In another embodiment of the wear testing device 1 illustrated in FIG. 4, a feeding mechanism 9 for feeding an interposing object W interposed between the test sample S and the circular circumferential surface 4a in contact with the test sample S is included. As for the interposing object W, under the condition in which rubber is used for the test sample S, materials or the like are used on the assumption that adhesion to the rubber occurs. As for the specific examples of the interposing object W, microscopic particles such as water, oil, and sand are included.

A difference in the wear state of the test sample S due to presence or absence of the interposing object W can be determined by providing the feeding mechanism 9. Consequently, it is much more advantageous to determine the wear state of rubber with accuracy in accordance with practical use. The supply amount (supply speed) of the interposing object W is favorably controlled by the control unit 7.

The invention claimed is:

1. A rubber wear testing device comprising:
    a holding unit configured to hold a test sample of rubber without rotating the test sample;
    a rotation body including a circular circumferential surface in contact with the test sample;
    a drive unit configured to drive and rotate the rotation body; and
    a compression bonding mechanism configured to apply a force oriented to the circular circumferential surface to the test sample held by the holding unit and always allow movement of the test sample in a direction opposite to the force,
    wherein the test sample held, without rotating, by the holding unit with respect to the rotation body being driven and rotated is configured to be compressed and bonded to the circular circumferential surface at a predetermined fixed position; and
    wherein the test sample slides on the circular circumferential surface, repeating a process in which the test sample counteracts frictional force on the circular circumferential surface and is elastically deformed and a process in which the test sample cannot counteract the frictional force and elastic deformation is released.

2. The rubber wear testing device according to claim 1, further comprising a control unit configured to control a rotation speed of the rotation body and the force.

3. The rubber wear testing device according to claim 2, further comprising a dynamometer configured to measure energy required for driving and rotating the rotation body.

4. The rubber wear testing device according to claim 3, further comprising a temperature sensor configured to detect a temperature of at least one of the circular circumferential surface or the test sample.

5. The rubber wear testing device according to claim 4, further comprising a camera configured to take a photograph of the movement of the test sample.

6. The rubber wear testing device according to claim 5, further comprising a temperature control mechanism configured to adjust the temperature of the test sample.

7. The rubber wear testing device according to claim 6, further comprising a scraper configured to come into contact with the circular circumferential surface.

8. The rubber wear testing device according to claim 7, further comprising a feeding mechanism configured to feed an interposing object interposed between the test sample and the circular circumferential surface in contact with the test sample.

9. The rubber wear testing device according to claim 1, further comprising a dynamometer configured to measure energy required for driving and rotating the rotation body.

10. The rubber wear testing device according to claim 1, further comprising a temperature sensor configured to detect a temperature of at least one of the circular circumferential surface or the test sample.

11. The rubber wear testing device according to claim 1, further comprising a camera configured to take a photograph of the movement of the test sample.

12. The rubber wear testing device according to claim 1, further comprising a temperature control mechanism configured to adjust a temperature of the test sample.

13. The rubber wear testing device according to claim 1, further comprising a scraper configured to come into contact with the circular circumferential surface.

14. The rubber wear testing device according to claim 1, further comprising a feeding mechanism configured to feed an interposing object interposed between the test sample and the circular circumferential surface in contact with the test sample.

* * * * *